United States Patent [19]

Fehr et al.

[11] Patent Number: 5,015,625

[45] Date of Patent: May 14, 1991

[54] ALICYCLIC ESTERS AND THEIR USE AS PERFUMING INGREDIENTS

[75] Inventors: Charles Fehr, Versoix; José Galindo, Les Avanchets, both of Switzerland

[73] Assignee: Firmenich SA, Geneva, Switzerland

[21] Appl. No.: 460,429

[22] Filed: Jan. 3, 1990

[30] Foreign Application Priority Data

Jan. 18, 1989 [CH] Switzerland .......................... 150/89

[51] Int. Cl.$^5$ ............................................. A01N 7/46
[52] U.S. Cl. ................................. 512/24; 252/174.11; 252/8.6
[58] Field of Search ..................... 512/24, 22; 560/128; 252/174.11, 8.6

[56] References Cited

U.S. PATENT DOCUMENTS

| | | | |
|---|---|---|---|
| 4,144,199 | 3/1979 | Wille et al. | 512/24 |
| 4,375,001 | 2/1983 | Schenk, I | 512/24 |
| 4,392,976 | 7/1983 | Calderone et al. | 512/24 |
| 4,411,829 | 10/1983 | Schulte-Elte et al. | 512/24 |
| 4,439,353 | 3/1984 | Schenk, II | 512/24 |
| 4,704,477 | 11/1987 | Gebauer et al. | 512/24 |

OTHER PUBLICATIONS

Chem. Abst., vol. 95, #187,427g (1981).
Uneyama et al., Chem. Abst., vol. 104, #109,999z (1986).
Ito et al., Chem. Abst., vol. 93, #132,631m (1980).

*Primary Examiner*—James H. Reamer
*Attorney, Agent, or Firm*—Pennie & Edmonds

[57] ABSTRACT

The compounds of formula

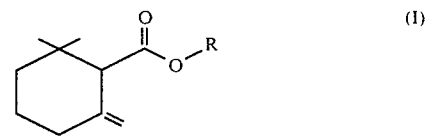

wherein the symbol R represents a linear or branched, saturated or unsaturated alkyl radical containing from 1 to 3 carbon atoms, are useful perfuming ingredients. They develop floral, rosy, damascone type odor notes and can therefore be used to confer, enhance, improve or modify the fragrance properties of perfuming compositions and perfumed articles.

Processes for the preparation of the compounds of formula (I) are also disclosed.

7 Claims, No Drawings

ALICYCLIC ESTERS AND THEIR USE AS PERFUMING INGREDIENTS

BRIEF SUMMARY OF THE INVENTION

The present invention relates to a method to confer, enhance, improve or modify the odor properties of a perfuming composition or a perfumed article, which method comprises adding to said composition or article a fragrance effective amount of a compound of formula

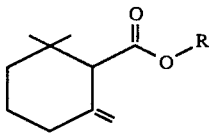

wherein the symbol R represents a linear or branched, saturated or unsaturated alkyl radical containing from 1 to 3 carbon atoms.

The invention further provides a perfuming composition and a perfumed article containing a compound of formula (I) as a perfuming ingredient.

Another object of the invention is a novel compound of formula

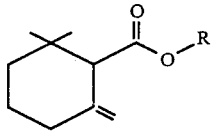

wherein the symbol R represents a n-propyl or an iso-propyl radical, or a linear or branched unsaturated alkyl radical containing 2 or 3 carbon atoms.

The invention also provides a process for the preparation of a compound of formula (I) as defined in claim 1, which process comprises the hydrolysis, by means of an aqueous solution of hydrochloric acid, of a compound of formula

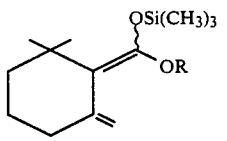

wherein the symbol R is defined as in claim 1.

A further object of the instant invention is another process for the preparation of a compound of formula (I) as defined in claim 8, which process comprises the reaction, in the presence of a basic agent, of 2,2-dimethyl-6-methylene-1-cyclohexanecarboxylic acid with an alkyl halide of formula RX, wherein the symbol R is defined as in claim 8 and the symbol X stands for a chlorine or a bromine atom, the reaction taking place in a solvent inert under the reactions conditions.

BACKGROUND OF THE INVENTION

Amongst the compounds of formula (I), methyl 2,2-dimethyl-6-methylene-1-cyclohexanecarboxylate and ethyl 2,2-dimethyl-6-methylene-1-cyclohexanecarboxylate are known chemical entities. They are in fact useful compounds in organic synthesis and, in particular, for the preparation of γ-damascone. Thus, the preparation and use of methyl 2,2-dimethyl-6-methylene-1-cyclohexanecarboxylate in this context has been described in the prior art [see, for example, R. L. Snowden, Helv. Chim. Acta, 71, 1587 (1988) and references therein] and namely in published European patent application No. 0260472. Likewise, published Japanese patent application No. 56-40633 has disclosed the preparation of γ-damascone starting from ethyl 2,2-dimethyl-6-methylene-1-cyclohexanecarboxylate. Nevertheless, the odor properties of these esters have remained unrecognized to this day.

THE INVENTION

We have now discovered that the compounds of formula (I) possess very interesting odor properties and that they can therefore be advantageously used for a wide range of applications in perfumery. This discovery is all the more unexpected in that the prior art already mentions the use in the fragrance industry of a wide variety of compounds having a chemical structure similar to that of the compounds of formula (I) (see, for example, European patent No. 0056109). One might therefore have expected that the compounds of the instant invention would have reproduced the olfactive patterns already known, bringing no new contribution to the perfumer's palette. Yet, not only did we find that the compounds of formula (I) have distinct odor qualities from those of the prior art compounds, but that their odor differs from one compound (I) to the next.

For example, methyl 2,2-dimethyl-6-methylene-1-cyclohexanecarboxylate, a preferred compound according to the invention, develops floral, rosy notes possessing a damascone type nuance, and a spicy-saffron side. Its odor note also possesses an herbaceous-thujonic connotation.

When compared to its α-isomer, i.e. methyl 2,6,6-trimethylcyclohex-2-ene-1-carboxylate, whose odor properties are described in European patent No. 0056109, the cited compound of the instant invention can be shown to possess a more floral and rosy note, and particularly more damascone-like than the note characterizing the α-isomer which is rather more herbaceous, camomile, camphoraceous-aromatic and not at all damascone-like. Furthermore, the odor note of methyl 2,2-dimethyl-6-methylene-1-cyclohexanecarboxylate is much more powerful than that of its α-isomer, a rather unexpected result if one considers that the opposite behavior is observed between α and γ-damascones.

Another preferred compound of the invention, ethyl 2,2-dimethyl-6-methylene-1-cyclohexanecarboxylate, develops a floral, rosy odor, with a less pronounced damascone character than that of its methyl ester homologue, but more metallic than the latter. On the other hand, the thujonic-absinthe side of the note is much more pronounced in the ethyl ester odor. When the latter is compared with the α-isomer of the methyl ester, or methyl 2,6,6-trimethylcyclohex-2-ene-1-cyclohexanecarboxylate, one can observe that ethyl 2,2-dimethyl-6-methylene-1-cyclohexanecarboxylate possesses a more camphoraceous, fruity, damascone-like and elegant odor note than that of said α-methyl ester.

The odor properties of other compounds (I) according to the invention are described in detail in the examples presented further on.

The compounds of formula (I) may be used for perfuming a great variety of products such as soaps, cosmetics, shampoos, deodorants, detergents and fabric softeners, as well as for the preparation of perfumes and perfuming bases. The use of these compounds in masculine type perfumes and Colognes is particularly advantageous.

They can be used in these applications in a wide range of concentrations, depending on the nature of the product to be perfumed and on the effect that is desired to achieve. For example, when used in the preparation of perfuming compositions, the compounds of the invention will be employed in concentrations varying typically from 0.5 to 10%, or even 20% by weight, relative to the weight of the composition. However, such values must not be interpreted in a restrictive manner, since they are known to be further dependent on the nature of the other coingredients in a given composition. In addition, the compounds of the invention may be used as the sole perfuming ingredient, or in admixture with other coingredients, solvents or the usual carriers.

From the preceding description, it comes out that the compounds of formula

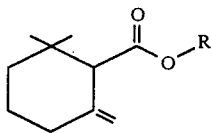

(I)

wherein the symbol R represents a n-propyl or an isopropyl radical, or a linear or branched unsaturated alkyl radical having from 1 to 3 carbon atoms, are novel chemical entities which are also the object of the present invention.

Both these compounds and the two esters whose structure is already known, i.e. methyl 2,2-dimethyl-6-methylene-1-cyclohexanecarboxylate and ethyl 2,2-dimethyl-6-methylene-1-cyclohexanecarboxylate, can be prepared starting from their β-isomers, according to an original process schematically represented as follows:

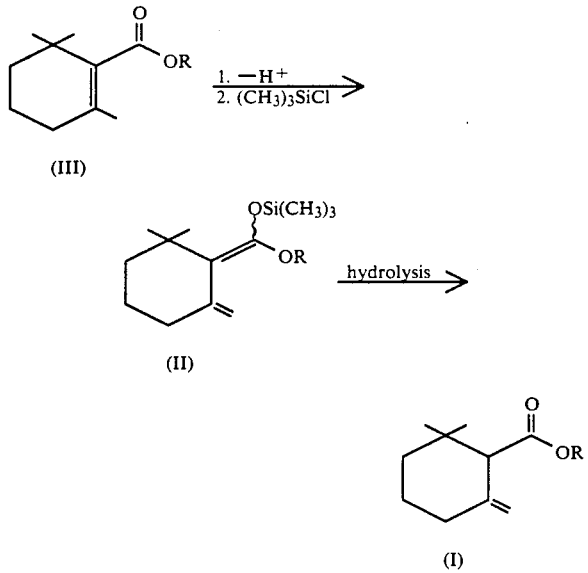

R defined as in claim 1.

The conditions of the reaction of deprotonation of ester (III), by means of a strong base, are described in European patent application No. 0260472. The addition of trimethylsilyl chloride to the reaction mixture yields the silyl derivative (II) whose acidic hydrolysis provides the desired γ-ester in high yields and free from its β-isomer. The present process has therefore the advantage of preventing the formation of mixtures of β- and γ-isomers, which is inevitable in the known processes of deconjugation of the double bond [see, for example, J. H. Posner et al., J. Am. Chem. Soc. 108, 7373 (1986)].

The hydrolysis reaction in the process represented above is carried out by means of an aqueous solution of hydrochloric acid.

Naturally, the esters of formula (I) can be derived from 2,2-dimethyl-6-methylene-1-cyclohexanecarboxylic acid according to processes which resort to the use of known or classical type reactions. For example, one such process in two steps, comprising the reaction of said acid with oxalyl chloride to yield an acyl chloride, which is then converted into the desired ester, is well documented in the literature [see, for example, J. March, Advanced Organic Chemistry, 3rd edition, pp. 346 and 388, John Wiley & Sons, USA (1985)].

Following another process according to the invention, compounds (I) can be prepared by an addition reaction analogous to the one described in European patent application No. 0178532, the teachings therein, relative to this reaction, being here included by reference. It is, in fact, the reaction, in the presence of a basic agent, of the above-mentioned carboxylic acid with an alkyl halide of formula XR, wherein R is defined as in claim 1 and X stands for a chlorine or bromine atom. As the basic agent in this reaction, potassium carbonate is preferentially used and the reaction takes place in a solvent inert under the reaction conditions, for example, acetone. This process is particularly adapted to the preparation of the esters of formula (I) containing an alkyl radical R which is not very bulky, such as the methyl, ethyl, propyl or allyl radicals.

The esters of formula (III) and the 2,2-dimethyl-6-methylene-1-cyclohexanecarboxylic acid, used as starting products in the processes described, are commercially available products or can be easily prepared by known methods.

The invention will now be described in greater detail by means of the following preparation examples, wherein temperatures are indicated in degrees centigrade and the abbreviations have the usual meaning in the art.

The invention will also be illustrated by means of examples concerning perfumery applications.

EXAMPLE 1

Preparation of methyl 2,2-dimethyl-6-methylene-1-cyclohexanecarboxylate

A solution of methyl 2,6,6-trimethyl-cyclohex-1-ene-carboxylate (80.0 g) in tetrahydrofuran (THF, 640 ml), contained in a 1.5 l flask equipped with a mechanical strirrer and a nitrogen inlet, was deprotonated by adding, between −10° and 0°, a solution of butyllithium in hexane (411 ml of a 1.5M solution). Once the addition was completed, the reaction was allowed to proceed at 15°-17° for 10 min. The temperature was reduced to −30° and trimethylsilyl chloride (143.35 g) was added to the reaction mixture over half an hour, while maintaining the temperature at 10° or below. The temperature was allowed to increase to 20° and the reaction mixture was poured on 5% HCl. After stirring for 10 min, the mixture was extracted with ether and the organic phase was washed with saturated aqueous solutions of $NaHCO_3$ and NaCl, dried over $Na_2SO_4$, filtered and the solvents evaporated. After distillation on a column filled with inox helices and equipped with a total reflux top, two fractions of a crude product were obtained.

Fraction 1: 51.04 g
Fraction 2: 5.86 g (GC: 88% pure)
Yield calculated on both fractions: 70%.

A further purification of this crude product provided the pure desired ester having B.p. 40°-50°/6.7 Pa. The analytical data are presented below.

IR: 1730, 1640, 1430, 1360, 1330, 1242, 1140, 1052, 1020, 892 $cm^{-1}$

NMR ($^1H$, 360 MHz): 0.93 (s, 3H); 0.97 (s, 3H); 1.24 (ddd, J=12.5, 5, 5 Hz, 1H); 1.59 (m, 2H); 1.84 (m, 1H); 2.11 (ddd, J=12.5, 5, 5 Hz, 1H); 2.47 (m, 1H); 2.88 (s, 1H); 3.65 (m, 1H); 4.73 (s, 1H); 4.85 (s, 1H) δ ppm NMR ($^{13}C$): 173.0 (s); 144.6 (s); 111.5 (t); 59.9 (d); 51.1 (q); 35.8 (t); 34.6 (s); 32.1 (t); 27.5 (q); 26.5 (q); 22.8 (t) δ ppm MS: 182 (M+, 13), 167 (20), 122 (83), 114 (37), 107 (56), 91 (24), 81 (41), 69 (100).

EXAMPLE 2

Preparation of ethyl 2,2-dimethyl-6-methylene-1-cyclohexanecarboxylate

In a flask maintained under nitrogen and equipped with a mechanical stirrer, a suspension of $K_2CO_3$ (29.5 g, 0.241 mole) in an acetone (200 ml) solution of 2,2-dimethyl-6-methylene-1-cyclohexanecarboxylic acid (30.0 g, 0.179 ml) and ethyl bromide (23.3 g, 0.214 mole) was warmed up to reflux. After 2 h 30, the temperature was allowed to cool to 25° and the reaction mixture was poured on 5% NaOH, extracted with ether (twice), washed with $H_2O$ and sat. NaCl, dried over $Na_2SO_4$, filtered and the solvents evaporated. Distillation of the crude product yielded, at 90°/5.3×10² Pa, 32.3 g of the desired ester (yield: 92%).

IR: 2950, 1725, 1645, 1440, 1385, 1325, 1160 $cm^{-1}$

NMR ($^1H$, 60 MHz): 0.94 (s, 3H); 0.98 (s, 3H); 1.26 (t, J=7 Hz, 3H); 1.5-2.7 (m, 6H); 2.90 (s, 1H); 4.16 (d, J=7 Hz, 2H); 4.76 (s, 1H); 4.85 (s, 1H) δ ppm MS: 196 (M+, 8), 181 (13), 153 (10), 139 (17), 135 (15), 128 (17), 123 (83), 122 (100), 112 (25), 107 (58), 81 (55), 69 (60).

EXAMPLE 3

Preparation of n-propyl 2,2-dimethyl-6-methylene-1-cyclohexanecarboxylate

This compound was prepared following the method described in the preceding example, using 5.00 g (29.7 mmole) of acid, 4.92 g (35.6 mmole) of $K_2CO_3$, 4.38 g of propyl bromide and 90 ml of acetone. Bulb-to-bulb distillation of the crude product yielded, at 100°-120°/5.3×10² Pa, 5.9 g (yield 95%) of the above-mentioned propyl ester.

IR: 2950, 1735, 1650, 1450, 1180, 1145 $cm^{-1}$

NMR ($^1H$, 360 MHz): 0.94 (s, 3H); 0.95 (t, J=7 Hz, 3H); 0.99 (s, 3H); 1.25 (m, 1H); 1.53 (m, 1H); 1.65 (m, 3H); 1.85 (m, 1H); 2.12 (m, 1H); 2.48 (m, 1H); 2.88 (s, 1H); 4.02 (m, 2H); 4.75 (s, 1H); 4.85 (s, 1H) δ ppm MS: 210 (M+, 7), 168 (14), 153 (28), 123 (97), 122 (100), 111 (29), 107 (54), 100 (40), 81 (55), 69 (85).

Odor note: floral, rosy.

EXAMPLE 4

Preparation of isopropyl 2,2-dimethyl-6-methylene-1-cyclohexanecarboxylate

In a three-neck flask kept under nitrogen, a solution of oxalyl chloride (3.47 g, 27.4 mmole) in methylene chloride (35 ml) was added to a solution of 2,2-dimethyl-6-methylene-1-cyclohexane-carboxylic acid (2.86 g, 17.1 mmole) in methylene chloride (30 ml). The reaction mixture was heated to reflux until there was no longer any gas release. The solvent was distilled, and the product vacuum pumped (around 5.3×10² Pa) to remove the last traces of volatile materials. The acyl chloride thus obtained was dissolved in methylene chloride (40 ml) and treated with triethylamine (1.81 g, 17.9 mmole) and isopropyl alcohol (5.13 g, 85.5 mmole). After 15 h stirring at 25°, the organic phase was extracted with ether and treated in the usual way. Bulb-to-bulb distillation at 80°/6.7 Pa yielded 2.16 g (yield 60%) of the desired ester.

IR: 2950, 1730, 1645, 1450, 1385, 1360, 1160, 1105 $cm^{-1}$

NMR ($^1H$, 360 MHz): 0.94 (s, 3H); 0.99 (s, 3H); 1.23 (d, J=6.5 Hz, 3H); 1.25 (d, J=6.5 Hz, 3H); about 1.25 (m, 1H); 1.54 (m, 1H); 1.66 (m, 1H); 1.83 (m, 1H); 2.11 (m, 1H); 2.48 (m, 1H); 4.75 (s, 1H); 4.84 (s, 1H); 5.00 (h, J=6.5 Hz, 1H) δ ppm MS: 210 (M+, 5), 168 (57), 153 (35), 123 (100), 122 (54), 107 (38), 100 (34), 81 (65), 69 (94), 43 (67).

Odor note: floral, rosy.

EXAMPLE 5

Preparation of allyl 2,2-dimethyl-6-methylene-1-cyclohexanecarboxylate

A process analogous to that described in Example 2 was used, with 8.00 g (0.048 mole) of 2,2-dimethyl-6-methylene-1-cyclohexanecarboxylic acid, 7.90 g (0.057 mole) of $K_2CO_3$, 6.90 g (0.057 mole) of allyl bromide and 100 ml of acetone. After approximately 1 h 15 of reaction, the temperature was allowed to return to 25° and the organic phase was extracted in the usual way. Bulb-to-bulb distillation (100°-120°/5.3×10² Pa) gave 9.79 g (yield 98%) of the desired allyl ester.

IR: 3100, 2950, 1740, 1660, 1450, 1390, 1335, 1180 $cm^{-1}$

NMR ($^1H$, 360 MHz): 0.94 (s, 3H); 0.99 (s, 3H); 1.25 (m, 1H); 1.54 (m, 1H); 1.64 (m, 1H); 1.84 (m, 1H); 2.12 (m, 11H); 2.46 (m, 1H); 2.92 (s, 1H); 4.56 (d "split", J=5 Hz, 2H); 4.76 (s, 1H); 4.85 (s, 1H); 5.22 (d "split", J=10 Hz, 1H); 5.32 (d "split", J=18 Hz, 1H); 5.92 (ddd, J=18, 10 et 5 Hz, 1H) δ ppm MS: 208 (M+, 2), 167 (38), 149 (12), 139 (20), 123 (44), 121 (100), 107 (45), 93 (27), 81 (64), 69 (58).

Odor note: rosy, green, metallic, slightly allylic.

EXAMPLE 6

A base perfuming composition for a masculine Cologne was prepared by admixture of the following ingredients:

| Ingredients | Parts by weight |
| --- | --- |
| Absinthe essential oil | 200 |
| Isobornyl acetate | 300 |
| Hexylcinnamic aldehyde | 300 |
| 10%* Methylnonylacetaldehyde | 150 |
| 10%* AMBROX ® DL[(1)] | 100 |
| 10%* Methyl anthranilate | 500 |
| Synth. bergamot oil | 700 |

| Ingredients | Parts by weight |
| --- | --- |
| Allyl cyclohexylpropionate | 100 |
| Cedarleaf | 150 |
| Cedroxyde[(2)] | 500 |
| Pure citral | 100 |
| Citronellol | 500 |
| Coumarine | 200 |
| DIMETOL ®[(3)] | 200 |
| Estragole | 50 |
| GALAXOLIDE ®[(4)] 50 | 900 |
| Clove bud essential oil | 250 |
| 50%* Maroc oakmoss absolute | 200 |
| Sweet orange essential oil | 700 |
| Mandarin essential oil | 200 |
| Patchouli essential oil | 150 |
| Tyrol pine essential oil | 100 |
| Rosemary essential oil | 600 |
| SANDALORE ®[(5)] | 200 |
| 10%* Vanillin | 200 |
| VERTOFIX COEUR ®[(6)] | 1000 |
| 10%* Styrax essential oil | 500 |
| Tetrahydrolinalol | 400 |
| 10%* γ-Undecalactone | 250 |
| Total | 9700 |

*in dipropylene glycol (DIPG)
[(1)]tetramethyl-perhydronaphthofuran; origin: Firmenich SA
[(2)]trimethyl cyclododecatriene epoxyde; origin: Firmenich SA
[(3)]2,6-dimethyl-2-heptanol; origin: L. Givaudan SA
[(4)]1,3,4,6,7,8-hexahydro-4,6,6,7,8,8-hexamethyl-cyclopenta-γ-benzopyran; origin: IFF Inc.
[(5)]5-(2,2,3-trimethylcyclopent-3-enyl)-3-methylpentan-2-ol; origin: L. Givaudan SA
[(6)]origin: IFF Inc.

To this base composition which had a Cologne-aromatic, woody and spicy note, 300 parts by weight of methyl 2,2-dimethyl-6-methylene-1-cyclohexanecarboxylate were added. The new composition acquired then a more floral-fruity character, and a richer herbaceous note. The strength and volume of the composition were thus enhanced.

By adding the same amount of ethyl 2,2-dimethyl-6-methylene-1-cyclohexanecarboxylate to the base composition, a new composition was obtained having an enhanced herbaceous character, but a less pronounced floral-fruity character than that of the new composition described in the preceding paragraph.

EXAMPLE 7

A rose type base perfuming composition was prepared by admixing the following ingredients:

| Ingredients | Parts by Weight |
| --- | --- |
| Citronellol | 1500 |
| Phenylethyl alcohol | 2000 |
| 1%* Purified indol | 500 |
| Dimethylbenzylcarbinyl acetate | 500 |
| Linalol | 600 |
| Terpineol | 700 |
| 50%* Cinnamic alcohol | 1000 |
| LILIAL ®[(1)] | 300 |
| Hexyl salicylate | 300 |
| Rosinol | 200 |
| 10%* Decanal | 200 |
| Cyclamen aldehyde | 150 |
| Dimethyl phenylacetic aldehyde | 100 |
| Styrallyl acetate | 100 |
| 2%* 1-(3,3-dimethylcyclohex-6-en-1-yl)-pent-4-en-1-one | 100 |
| Hexylcinnamic aldehyde | 200 |
| Phenylethyl phenylacetate | 200 |
| 10%* ROSALVA ®[(2)] | 350 |
| Total | 9000 |

*in dipropylene glycol (DIPG)
[(1)]α-methyl-p-tert-butyl hydrocinnamic aldehyde; origin: L. Givaudan SA
[(2)]9-decen-1-ol; origin: IFF Inc.

500 parts by weight of methyl 2,2-dimethyl-6-methylene-1-cyclohexane carboxylate were added to this base composition. The resulting new composition developed a distinctly more rose petal character, more fruity in the direction of damascone. Furthermore, the new composition had a much more powerful odor.

What is claim is:

1. A method to confer, enhance, improve or modify the odor properties of a perfuming composition or a perfumed article, which method comprises adding to said composition or article a fragrance effective amount of a compound of formula

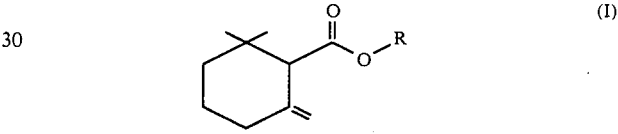

wherein the symbol R represents a linear or branched, saturated or unsaturated alkyl radical containing from 1 to 3 carbon atoms so as to impart a floral, rosy, damascone type odor note to said composition or article.

2. A method according to claim 1, wherein the compound of formula (I) is methyl 2,2-dimethyl-6-methylene-1-cyclohexanecarboxylate or ethyl 2,2-dimethyl-6-methylene-1-cyclohexanecarboxylate.

3. A perfuming composition containing a compound of formula (I) as defined in claim 1 as a perfuming ingredient.

4. A perfuming composition according to claim 3, wherein the said compound of formula (I) is methyl 2,2-dimethyl-6-methylene-1-cyclohexanecarboxylate or ethyl 2,2-dimethyl-6-methylene-1-cyclohexanecarboxylate.

5. A perfumed article containing a compound of formula (I) as defined in claim 1 as a perfuming ingredient.

6. A perfumed article according to claim 5, wherein the said compound of formula (I) is methyl 2,2-dimethyl-6-methylene-1-cyclohexanecarboxylate or ethyl 2,2-dimethyl-6-methylene-1-cyclohexanecarboxylate.

7. A soap, a bath or shower gel, a shampoo, a cosmetic preparation, a body deodorizer, a detergent or a fabric softener, a perfume or a Cologne, as perfumed article according to claim 5 or 6.

* * * * *